United States Patent [19]

Tamaoki et al.

[11] Patent Number: 5,236,929
[45] Date of Patent: Aug. 17, 1993

[54] COMPOUND UCA1064-B

[75] Inventors: Tatsuya Tamaoki, Machida; Isami Takahashi, Tama; Katsuhiko Ando, Machida; Mayumi Yoshida, Sagamihara; Toshiaki Iwazaki, Shizuoka, all of Japan

[73] Assignee: Kyowa Hakko Kogyo Co., Ltd., Tokyo, Japan

[21] Appl. No.: 847,279

[22] Filed: Mar. 10, 1992

[30] Foreign Application Priority Data

Mar. 13, 1991 [JP] Japan ................................ 3-048206

[51] Int. Cl.$^5$ .......................................... C07D 215/12
[52] U.S. Cl. ..................................... 514/284; 546/77; 435/127
[58] Field of Search .......................... 546/77; 514/284

[56] References Cited

U.S. PATENT DOCUMENTS

| | | | |
|---|---|---|---|
| 3,887,564 | 6/1975 | Williams et al. | 546/77 |
| 3,972,884 | 8/1976 | Jones | 546/77 |
| 4,008,238 | 2/1977 | Jones | 546/77 |
| 4,039,547 | 8/1977 | Chamberlin | 546/77 |

OTHER PUBLICATIONS

Folkman et al., Science, vol. 221, pp. 719-725 (1983).
Mori et al., Heterocycles, vol. 24, pp. 1257-1260 (1986).
"Multidisciplinary Study of Rio Flavor in Brazilian Green Coffee", p. 785, vol. 115, No. 11, Sep. 16, 1991, Columbus, Ohio, Abstract No. 113248.
"Influence of Solute, pH, and Incubation Temperature on Recovery of Heat-Stressed Wallemia-sebi Conidia", vol. 113, No. 19, Nov. 5, 1990, Columbus, Ohio, Abstract No. 170561, p. 582.
"Study on a Toxic Metabolite from the Mold Wallemia", vol. 112, No. 17 Apr. 23, 1990, Columbus, Ohio, Abstract No. 153394, p. 243.
"Affects of Water Activity and Culture Age on the Glycerol Accumulation Patterns of Five Fungi", vol. 104, No. 19, May 12, 1986; Columbus, Ohio, Abstract No. 165010, p. 351.
"Natural-Abundance Carbon-13 Nuclear Magnetic Resonance Studies on the Internal Solutes of Xerophilic Fungi", vol. 99, No. 23, Dec. 5, 1983, Columbus, Ohio, Abstract No. 191221, p. 433.
Journal of the Chemical Society Perkin Transaction I, No. 13, 1973, Letchworth, G.B., pp. 1416-1424, "Natural and Synthetic Pyrrol-2-ylpolyenes".
Journal of Antibiotics, vol. 27, No. 12, Dec. 1974, Tokyo, JP, pp. 992-993; J. W. Chamberlin et al., "Structure of Antibiotic", A-25822-B, A Novel Nitrogen-Containing C28-Sterol with Anti-Fungal Properties.

*Primary Examiner*—Donald G. Daus
*Attorney, Agent, or Firm*—Antonelli, Terry, Stout & Kraus

[57] ABSTRACT

Disclosed is UCA1064-B, a compound represented by formula (I):

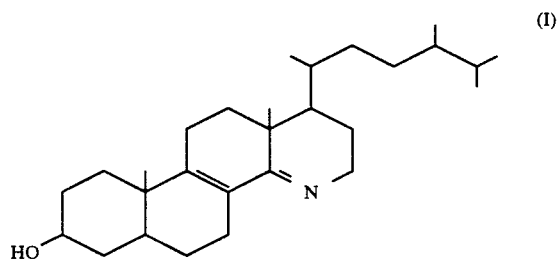

and having an antibacterial, antifungal and anti-tumor activity. UCA1064-B is produced by culturing a microorganism belonging to the genus Wallemia.

2 Claims, No Drawings

COMPOUND UCA1064-B

BACKGROUND OF THE INVENTION

The present invention relates to a compound designated as UCA1064-B. UCA1064-B has an antibacterial, antifungal and anti-tumor activity and is useful as an antibacterial, antifungal and anti-tumor agent.

As a compound structurally similar to the compound of the present invention, Compound A25822B represented by formula (II):

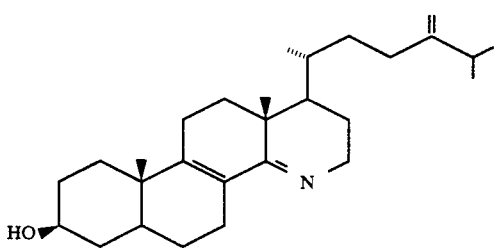

(II)

is known [THE JOURNAL OF ANTIBIOTICS, 27(12), 992 (1974)]. However, there is no report that Compound A25822B has an anti-tumor activity.

SUMMARY OF THE INVENTION

The present invention provides a compound designated as UCA1064-B and represented by formula (I):

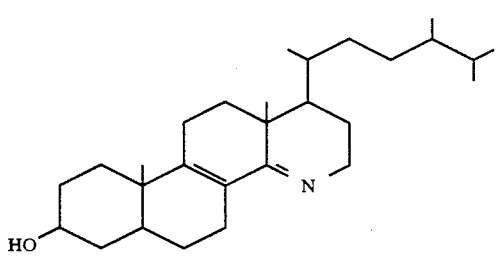

(I)

The compound can be obtained by culturing a microorganism belonging to the genus Wallemia.

DETAILED DESCRIPTION OF THE INVENTION

It has been found that a substance having an antibacterial, antifungal and anti-tumor activity is produced in the culture obtained by culturing a microorganism isolated from commercially available dried sweet potato in a medium. After isolation and purification of the substance, its physicochemical properties were studied, whereby it has been found to be a novel substance. The substance has been named UCA1064-B.

The physicochemical properties of UCA1064-B are given below.

(i) Appearance: white powder
(ii) Molecular formula: $C_{28}H_{47}NO$
(iii) Molecular weight: 413
(iv) Mass spectrum: SIMS 414 $(M+1)^+$, EIMS 413 $(M+1)^+$
(v) Specific rotation: $[\alpha]_D^{24} = -28.5°$ (c=0.5, methanol)
(vi) UV absorption spectrum (methanol solution) λmax nm (ε): 279 (8,700) (under acidic conditions) 241 (7,500) (under basic conditions)
(vii) IR absorption spectrum (chloroform solution) $\nu(cm^{-1})$: 3400, 2950, 1690, 1610, 1450, 1370, 1070
(viii) $^1$H-NMR (500 MHz, CDCl$_3$) (δ) 3.97 (1 H), 3.64 (1 H), 3.50 (1 H), 1.03 (3 H, s), 0.95 (3 H, s), 0.93 (3 H, d, J=6.9 Hz), 0.86 (3 H, d, J=6.8 Hz), 0.79 (3 H, d, J=6.8 Hz), 0.77 (3 H, d, J=6.8 Hz)
(ix) $^{13}$C-NMR (100 MHz, CDCl$_3$) (δ) 172.7 (s), 147.3 (s), 127.5 (s), 70.9 (d), 51.2 (t), 48.3 (d), 40.7 (d), 39.0 (d), 38.2 (t), 37.7 (s), 37.2 (s), 34.9 (t), 33.4 (t), 33.4 (t), 31.7 (d), 31.6 (d), 31.5 (t), 30.5 (t), 27.2 (t), 25.5 (t), 21.7 (q), 20.7 (t), 20.4 (q), 19.2 (t), 18.5 (q), 17.8 (q), 16.8 (q), 15.5 (q)
(x) Color reaction: positive to vanillin sulfate and iodine tests
(xi) Solubility: soluble in alcohol, acetone, ethyl acetate and chloroform; insoluble in water and hexane
(xii) Silica gel thin layer chromatography (TLC):
  Thin layer: Art. 5715 manufactured by Merck & Co.
  Developing solvent: chloroform:methanol=85:15
  Rf value: 0.35
(xiii) High performance liquid chromatography (HPLC):
  Column: Wako sil 5C18 (Wako Pure Chemical Industries, Ltd.)
  Flow rate: 1 ml/min
  Mobile phase: 80% methanol [10 mM citrate-phosphate buffer solution (pH 4.0)]
  Retention time: 13.5 min.

The biological activities of UCA1064-B are described below.

(A) Antibacterial and Antifungal Activity

The minimum inhibitory concentration (MIC) of UCA1064-B against various bacteria and fungi was determined by the agar dilution method using a medium (pH 7) prepared by dissolving 3 g of Bacto-Tryptone (Difco Laboratories), 3 g of meat extract, 1 g of yeast extract, 1 g of glucose and 16 g of agar in 1 liter of water. The result is shown in Table 1.

TABLE 1

| Bacteria Tested | Minimum Inhibitory Concentration (μg/ml) |
|---|---|
| Candida krusei MTU12041 | 0.78 |
| Saccharomyces cerevisiae MTU09001 | 0.39 |
| Staphylococcus aureus ATCC6538P | 20.0 |
| Enterococcus faecium ATCC10541 | 40.0 |
| Bacillus subtilis No. 10707 | 20.0 |
| Klebsiella pneumoniae ATCC10031 | >100 |
| Salmonella typhi ATCC9992 | >100 |

(B) Growth Inhibition Against BALB 3T3 Cells Transformed by the Oncogene H-Ras (Hereinafter Referred to as BALB 3T3/H-Ras Cells)

A BALB 3T3/H-ras cell suspension ($3 \times 10^4$ cells/ml) prepared by suspending BALB 3T3/H-ras cells in a medium comprising DME medium (Nissui Pharmaceutical Co, Ltd.) and 10% fetal calf serum (hereinafter referred to as Medium A) was put into wells of a 96-well microtiter plate in an amount of 0.1 ml per well. After the plate was incubated at 37° C. for 20 hours in a CO$_2$- incubator, 0.1 ml of a sample of UCA1064-B appropriately diluted with Medium A was added to each well. The cells were further incubated at 37° C. for 72 hours in the $CO_2$-incubator. After the culture supernatant was removed, the residue was washed once with physiological saline and then treated with 0.1 ml of methanol for 10 minutes to fix the cells. The cells were stained with 0.1 ml of Giemsa's staining solution [Giemsa's staining solution, Merck Art 9204 (Merck & Co.): physiological saline=1:10]for 5 minutes. After the staining solution was removed, the residue was washed once with 0.2 ml of water. Then, the dye was extracted with 0.2 ml of 0.1N hydrochloric acid and absorbance was measured at 620 nm with a microplate reader. The concentration of the test compound at which the growth of the cells is inhibited by 50% ($IC_{50}$) was calculated by comparing the absorbance of intact cells with those of the cells treated with the test compound at known concentrations.

The result is shown in Table 2.

TABLE 2

| Test Compound | BALB 3T3/H-ras Inhibition Activity $IC_{50}$ (μg/ml) |
| --- | --- |
| UCA1064-B | 3.5 |

(C) Anti-Tumor Activity Against Mouse Mammary Cancer SC-4

Mouse mammary cancer SC-4 (8 $mm^3$) was subcutaneously implanted into BALB/c nu/nu nude mice (5-weeks-old, male) at ventral side using a trockar.

After the volume of the tumor reached 100-300 $mm^3$, UCA1064-B was subcutaneously administered near the tumor at a dose of 15 mg/kg once a day for 4 days. UCA1064-B was administered in the form of a suspension, which was prepared by triturating 10 mg of UCA1064-B with 20 μl of Tween 80 and then suspending the compound in 0.3% carboxymethyl cellulose (CMC).

For comparison, 100 mg/kg of cortisone was subcutaneously administered once a day for 5 days in a similar manner.

Five days after the start of administration, the anti-tumor activity was determined as T/C (T: the volume of the tumor of the test group, C: the volume of the tumor of the control group).

The result is shown in Table 3.

TABLE 3

| Compound | Dose (mg/kg) | T/C |
| --- | --- | --- |
| UCA1064-B | 15 × 4 | 0.49* |
| Cortisone | 100 × 5 | 0.39** |

Note)
*$P < 0.01$
**$P < 0.05$
by Mann-Whitney's U-test [S. Ishii, SEIBUTSUTOKEIGAKU NYUMON (Introduction to Biostatistics) p. 109, Baifukan[

The results shown above reveal that UCA1064-B inhibits the growth of cancer cells.

The process for producing UCA1064-B is described below.

UCA1064-B can be obtained by culturing a microorganism belonging to the genus Wallemia and having the ability to produce UCA1064-B in a medium, allowing UCA1064-B to accumulate in the culture, and recovering UCA1064-B from the culture.

Any strain may be used as long as it belongs to the genus Wallemia and has the ability to produce UCA1064-B. Further, mutants derived from such strains by artificial mutation, e.g., by Uv irradiation, X-ray irradiation and treatment with a mutagen or by spontaneous mutation may be used as long as they are capable of producing UCA1064-B. A representative strain is *Wallemia sebi* KAC-1341 strain (hereinafter referred to as KAC-1341 strain).

The mycological properties of KAC-1341 strain are described below.

(1) Macroscopic observation

When KAC-1341 strain is cultured at 25° C. on a malt extract agar medium, the diameter of a colony reaches 6-9 mm on the fourteenth day of incubation. The surface of the colony is dull light red and the reverse side is dark brown. The periphery of the colony shows a brownish cream color.

When the strain is cultured at 25° C. on a potato glucose agar medium, the diameter of a colony reaches 6-11 mm on the fourteenth day of incubation. The surface of the colony is light brownish tan and the reverse side is greyish black. The periphery of the colony shows a cream color.

When the strain is cultured at 25° C. on a 40% sucrose-supplemented malt extract-yeast extract agar medium [Harrold's M40Y], the diameter of a colony reaches 11-15 mm on the fourteenth day of incubation. The surface of the colony is greyish light red and the reverse side is brown. The periphery of the colony shows a light brown color.

The optimum growth temperature for this strain is in the range of 12 to 30° C. The strain grows best at about 25° C. The pH range which allows its growth is 4 to 7 and the optimum growth pH is 5.5 to 6.5.

(2) Optical microscopic observation of the strain when cultured on a 40% sucrose-supplemented malt extract-yeast extract agar medium Hyphae are septate, colorless and smooth and branch well. Conidiophores singly arise from the hyphae to form cylindrical or lageniform conidiogenous cells. The conidiogenous cells sometimes show apical growth repeatedly to form a long conidiophore. Cylindrical conidial primordium extends from the pointed end of the conidiogenous cell. The conidial primordium is about 30 μm long and 2-2.5 μm wide, and is somewhat thick at the base (2.5-3.0 μm wide). Septa are formed from the tip of the conidial primordium to the base thereof 1.5-2.5 μm apart from one another and cells finally divide at the septa into single cell arthroconidia. The arthroconidium is colorless, smooth and quadrangular at the beginning and as it matures, becomes light brown and the surface slightly becomes spinulose or verrucose and the shape changes to globose or subglobose. The matured conidium has a diameter of 2.5-3.5 μm and the wall is somewhat thick. In this strain, the foregoing anamorph alone is observed and no teleomorph is observed.

Taxonomical study of this strain based on the above mycological properties was made according to M. B. Ellis, DEMATIACEOUS HYPHOMYCETES, 37-38 (1971), and as the result, the strain was identified as *Wallemia sebi* (Fries) von Arx. The strain was named *Wallemia sebi* KAC-1341 strain and was deposited with the Fermentation Research Institute, Agency of Industrial Science and Technology, Japan as FERM BP-3270 on Feb. 12, 1991 under the Budapest Treaty.

For incubation of the UCA1064-B-producing strains of the present invention, conventional methods for culturing fungi are generally used. As the medium, any of synthetic media and natural media may be used as far as it appropriately contains carbon sources, nitrogen sources, inorganic substances, etc. which can be assimilated by the strain used.

As the carbon sources, glucose, starch, dextrin, mannose, sucrose, lactose, xylose, arabinose, mannitol, molasses, etc., can be used singly or in combination. Hydrocarbons, alcohols, organic acids, and the like may also be used depending upon the assimilation ability of the strain. As the nitrogen sources, ammonium chloride, ammonium sulfate, ammonium nitrate, sodium nitrate, urea, peptone, meat extract, yeast extract, dry yeast, corn steep liquor, soybean powder, Casamino acid, etc., can be used singly or in combination. In addition, inorganic salts such as sodium chloride, potassium chloride, magnesium sulfate, calcium carbonate, potassium dihydrogenphosphate, dipotassium hydrogenphosphate, ferrous sulfate, calcium chloride, manganese sulfate, zinc sulfate, copper sulfate, etc. may also be added, if necessary. Furthermore, substances which can accelerate the growth of the strain used or the production of UCA1064-B, for example, vitamin $B_1$ and biotin, may also be added.

The incubation may be carried out by liquid culture or solid culture, but is usually carried out by liquid culture, especially submerged stirring culture, at a temperature of 16° to 37° C., preferably 25° to 32° C., and at pH 4 to 10, preferably 6 to 8. The desired substance UCA1064-B is produced and accumulated in the culture broth and the cells usually by incubation for 1 to 7 days. During the incubation, the pH of the medium is adjusted by using aqueous ammonia or aqueous ammonium carbonate. When the amount of UCA1064-B formed in the culture reaches the maximum, the incubation is discontinued and UCA1064-B is isolated and purified from the culture.

UCA1064-B is isolated and purified from the culture by a method conventionally used for isolating and purifying a metabolite of a microorganism from the culture. For example, the culture is separated into cell-free culture broth and microbial cells by filtration or centrifugation. The cells are then extracted with chloroform, acetone, or the like. Thereafter, the extract is combined with the cell-free culture broth and the mixture is passed through a column packed with a polystyrene type adsorbent resin, e.g., DIAION HP20 (Mitsubishi Kasei Corporation) to adsorb the active component onto the resin. Alternatively, the culture may be extracted with a solvent such as chloroform, acetone or n-propanol, followed by removal of the microbial cells by filtration and treatment of the filtrate with a polystyrene type adsorbent resin such as DIAION HP20. The active component adsorbed on the resin is eluted with ethyl acetate, acetone, methanol, or the like. The eluate is concentrated and the concentrate is subjected to silica gel column chromatography, high performance liquid chromatography, or the like to obtain UCA1064-B as white powder. During the incubation and purification steps, UCA1064-B can be traced by high performance liquid chromatography.

When UCA1064-B is used as an anti-tumor composition, the compound is dissolved in physiological saline or a solution of glucose, lactose or mannitol for injection, and usually intravenously administered as an injection in a dose of 0.1 to 100 mg/kg. Alternatively, the compound may be freeze-dried in accordance with the Japanese Pharmacopoeia or may be prepared into injectable powder by adding sodium chloride thereto. Further, the anti-tumor composition may also contain pharmaceutically acceptable well-known diluents, adjuvants and/or carriers such as salts which satisfy requirements for medical use. In cases where the compound is used as an injection, it is sometimes preferred to use auxiliary agents which enhance the solubility. Doses may be appropriately varied depending upon the age and conditions. Administration schedule can also be varied depending upon the conditions and dose. For example, the compound is administered once a day (by single administration or consecutive administration) or intermittently by one to three times a week or once every three weeks. Further, oral administration and rectal administration are also possible in the same dose and in the same manner. The compound can be administered, with appropriate adjuvants, as tablets, powders, granules, syrup, etc. for oral administration and as suppositories for rectal administration.

Certain embodiments of the invention are illustrated in the following representative examples.

EXAMPLE 1

*Wallemia sebi* KAC-1341 strain (FERM BP-3270) was used as the seed strain. The strain was inoculated into 300 ml of a seed medium (pH 6.0 prior to sterilization) comprising 200 g/L V8 vegetable juice (Campbell Japan) and 30 g/L sucrose in a 2-L Erlenmeyer flask, followed by shaking culture (200 rpm) at 25° C. for 96 hours.

The resulting seed culture was transferred into 15 L of a medium having the same composition as described above in a 30-L jar fermentor in the rate of 5% (volume). Incubation was carried out at 25° C. for 96 hours with stirring (rotation: 200 rpm, aeration: 15 L/min). The thus obtained culture was transferred into 100 L of a medium having the same composition as described above in a 200-L fermentor tank in the rate of 10% (volume). Incubation was carried out at 25° C. for 96 hours with stirring. The obtained culture was transferred into 1000 L of a fermentation medium having the following composition in a 2000-L fermentor tank in the rate of 10% (volume). Incubation was carried out at 25° C. with stirring.

Composition of the fermentation medium:
60 g/L sucrose, 30 g/L yeast extract, 0.5 g/L $KH_2PO_4$, 0.5 g/L $MgSO_4 \cdot 7H_2O$ (pH 6.0 prior to sterilization)

The incubation was carried out for 96 hours without particularly adjusting the pH of the medium. After completion of incubation, 500 L of n-propanol was added to the culture, followed by stirring. The cells and precipitates were filtered off from the culture to obtain 1500 L of a filtrate.

After being adjusted to pH 8.0, the filtrate was passed through a column packed with the polystyrene type adsorbent resin DIAION HP20 (50 L) to adsorb the active substance on the resin. Impurities were eluted with deionized water and 30% methanol, and then the active substance was eluted with 100% methanol. After the active fraction was concentrated, water was added to adjust the pH to 10.0, followed by extraction with ethyl acetate. Concentration of the ethyl acetate layer gave 100 g of a brown oily substance. The brown oily substance was applied to a column packed with silica gel (Art. 7734; Merck & Co.). After impurities were eluted with chloroform and then with a solvent mixture of chloroform and methanol (9:1), the active substance was eluted with a solvent mixture of chloroform and methanol (8:2). The fraction containing the active substance was concentrated, and the resulting substance was passed through a column packed with silica gel (Art. 9390 Lichroprep Si60; Merck & Co.), followed by elution with chloroform and then with a solvent mixture of chloroform and methanol (8:2). The active fraction was concentrated and the concentrate was subjected to high performance liquid chromatography with 80% methanol (citrate-phosphate buffer, pH 4.0) as the eluent using reversed phase silica gel (YMC ODS SH-363-5; YMC Co.), whereby 100 mg of UCA1064-B was obtained as white powder.

EXAMPLE 2

The same procedure as in Example 1 was repeated except that a fermentation medium having the following composition was used. As the result, 60 mg of UCA1064-B was obtained as white powder.

Composition of the fermentation medium:
60 g/L glucose, 30 g/L yeast extract, 0.5 g/L $KH_2PO_4$, 0.5 g/L $MgSO_4.7H_2O$ (pH 6.0 prior to sterilization)

What is claimed is:

1. UCA1064-B, a compound represented by formula (I):

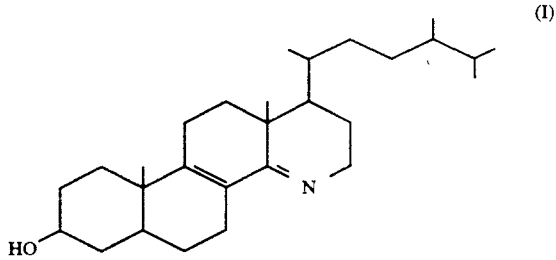

2. A pharmaceutical composition comprising a pharmaceutical carrier and as an active ingredient, an effective amount of UCA1064-B.

* * * * *